United States Patent [19]

Ereren

[11] Patent Number: 5,273,055
[45] Date of Patent: Dec. 28, 1993

[54] PROTECTIVE SHIELD FOR INTRATHORACIC/INTRA-ABDOMINAL LAPAROSCOPIC MEDICAL PROCEDURES

[76] Inventor: Erkan Ereren, 2554 N. Meridian Dr., Orange, Calif. 92667

[21] Appl. No.: 989,529

[22] Filed: Dec. 11, 1992

[51] Int. Cl.⁵ .................. A61F 5/37; A61F 13/00; A61B 19/00
[52] U.S. Cl. .................. 128/846; 128/849; 128/888
[58] Field of Search ............... 128/849–856, 128/888, 889; 606/144, 215, 216, 233; 600/37; 602/41, 42, 48, 59

[56] References Cited

U.S. PATENT DOCUMENTS

| | | | |
|---|---|---|---|
| 2,835,253 | 5/1958 | Borgeson | 128/850 |
| 3,332,417 | 7/1967 | Blanford | 128/850 |
| 3,347,226 | 10/1967 | Harrower | 128/850 |
| 3,347,227 | 10/1967 | Harrower | 128/850 |
| 3,397,692 | 8/1968 | Creager | 128/850 |
| 3,416,520 | 12/1968 | Creager | 128/850 |
| 3,863,639 | 2/1975 | Kleaveland | 128/850 |
| 4,271,828 | 6/1981 | Angelchik | 600/37 |
| 4,865,032 | 9/1989 | Jones | 606/144 |
| 5,082,005 | 1/1992 | Kaldany | 128/850 |

*Primary Examiner*—Michael A. Brown
*Attorney, Agent, or Firm*—G. Donald Weber, Jr.

[57] ABSTRACT

A shield formed of a thin, flexible, spreadable sheet having approximate sizes and shapes. The sheet can include pockets for receiving miscellaneous materials, as well as a handle for easy extraction from an intrabody cavity. The shields are made of non-flammable, non-toxic materials and are used in laparoscopic procedures.

5 Claims, 1 Drawing Sheet

PROTECTIVE SHIELD FOR INTRATHORACIC/INTRA-ABDOMINAL LAPAROSCOPIC MEDICAL PROCEDURES

BACKGROUND

1. Field of the Invention

This invention is directed to medical devices, in general, and to a medical device, namely a shield, used in laparoscopic medical procedures, in particular.

2. Prior Art

There are many known medical tools, instruments and accessories now on the market. Many of these devices are used in conjunction with surgical procedures.

One of the new types of surgical procedures is the laparoscopic and/or thorascoscopic procedure. These types of surgeries are relatively recent advances in abdominal, pelvic and/or chest surgeries wherein a surgical procedure is performed in a body cavity.

In laparoscopic procedures, unlike traditional surgery, there is no large incision made in the body. Rather, laparoscopic types of surgeries are performed by placing small-sized tubing, for example, on the order of 5mm, 10mm and/or 12mm diameter, through puncture-type wounds of the abdominal, pelvic and/or chest cavities. The surgical instrument is then inserted through the tube (frequently referred to as a cannula) in order to perform the surgery.

Of course, other cannulas can be used for insertion of fiber optic light sources and/or cameras in order for the surgeon to view the interior of the cavity.

During such surgeries, the surgical instruments are also inserted through cannulas to perform the procedures within the body cavity.

Many of the instruments utilized in the procedures include sharp portions which could, inadvertently, create an internal injury. Conversely, some of the instruments are relatively blunt, but could produce trauma during the procedures.

On the other hand, many of the organs which are in the vicinity and/or proximity of the underlying surgical procedure have no problems It is highly desirable not to inflict any such problems to the organs during the procedure.

In like fashion, during such procedures, infectious materials can be discharged from diseased tissue; blood can be discharged; irrigation solutions can be required; and, as well, portions of the internal organs may be removed. It is highly desirable to be able to control the disposition of any irrigation fluids, blood, body parts and the like which are generated during these surgical procedures and, as well, protect any of the body parts which are not included in the underlying procedure. However, until the present, there has been no specific component which provides these advantages.

PRIOR ART STATEMENT

During a preliminary patentability search, the following patents were uncovered.

U.S. Pat. No. 1,275,520; GAUZE DAM SURGICAL INSTRUMENT; Bell. This patent is directed to a gauze dam for controlling the internal organs during abdominal operations or procedures.

U.S. Pat. No. 1,947,649; SURGICAL INSTRUMENT; Kadavy. This patent is directed to an instrument for retaining the abdominal viscera away from a wound while suturing the peritoneum.

U.S. Pat. No. 3,435,821; SURGICAL DRAPE; Bennett. This patent is directed to a surgical drape that is easily and quickly positioned in and about a body cavity during an operation and including means for closing the open ends of severed tubes in the abdominal cavity to prevent the flow of fluids out of the tubes and into the cavity.

U.S. Pat. No. 3,863,639; DISPOSABLE VISCERAL RETAINER; Kleaveland. This patent is directed to a collapsible, disposable retainer device for insertion beneath an abdominal incision for temporarily retaining the viscera inside the abdominal cavity and includes a peripheral, tubular, inflatable bladder.

U.S. Pat. No. 4,217,890; SURGICAL SLING FOR POSITIONING A HARVESTED KIDNEY DURING SURGICAL REATTACHMENT; Owens. This patent is directed to a method and apparatus comprising a non-wettable material sling in the general shape of a kidney.

U.S. Pat. No. 4,865,032; FABRIC AND METHOD OF USE FOR TREATMENT OF SCARS; O,Keeffe. This patent is directed to a method for implantation beneath or within the dermis to control formation of scar tissue.

U.S. Pat. No. 4,947,843; CARDIAC INSULATOR; Wright et al. This patent is directed to a disposable cardiac insulator to thermally insulate the myocardium from the pericardial cavity during bypass procedures.

U.S. Pat. No. 4,964,414; ELECTRODE FOR USE IN IMPLANTING IN A LIVING BODY; Handa et al. This patent is directed to an electrode which is implanted in a living body and is used for electrical stimulation of paralyzed muscles.

U.S. Pat. No. 5,037,428; VESSEL APPROXIMATION AND ALIGNMENT DEVICE; Picha et al. This patent is directed to a T-shaped device which is adapted to fit within the end of vessel segments which are to be anastomosed.

U.S. Pat. No. 5,057,117; METHOD AND APPARATUS FOR HEMOSTASIS AND COMPARTMENTALIZATION OF A BLEEDING INTERNAL BODILY ORGAN; Atweh. This patent is directed to an apparatus for compartmentalizing and carrying out hemostasis of a massively bleeding internal bodily organ.

U.S. Pat. No. 5,084,061; INTRAGASTRIC BALLOON WITH IMPROVED VALVE LOCATING MEANS; Gau et al. This patent is directed to an ellipsoid-shaped balloon which can be implanted in the stomach having a filler valve and a retrievable tab thereon.

DESCRIPTION OF A PREFERRED EMBODIMENT

Figure 1:
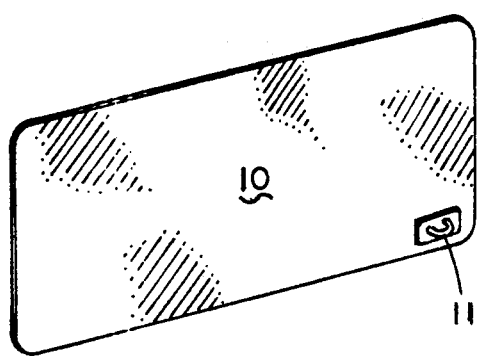
FIG. 1 is an isometric view of a generally rectilinear shield in accordance with the instant invention.

Referring now to FIG. 1, there is shown an embodiment of the instant invention. In this embodiment, a shield 10 is of a generally rectilinear configuration. By rectilinear, in this instance, is meant a rectangular, square, elliptical or any other generally planar shield. In this instance, a more rectangular configuration is shown. However, it must be understood that the corners can be rounded; the ends tapered; and so forth. The shield 10 comprises a thin membrane-like material such as polypropylene or other similar type of materials. Polypropylene is merely one example of a useful material and is not limitative of the invention. The material must be non-toxic and should not interact with or react to any of the internal bodily fluids or any of the materials which are to be utilized by a surgeon during a surgical procedure. Preferably, the material of the shield should be able to protect tissue and/or organs from injury by laser or electrocauterizing devices. Some representative dimensions of the shield 10 are approximately 10-20 inches long by 5-10 inches wide by ½-2 millimeters thick. The material can be transparent, translucent or opaque, as deemed appropriate.

In addition, the material should be FDA approved to be used during medical or surgical procedures and should have all other attributes of being non-invasive and non-traumatic when placed within a body cavity.

Also, secured to one surface of the shield 10 is a handle 11, which is used during the insertion and/or retrieval of the shield.

In the instant case, the handle 11 takes the form of a small tab or loop which extends outwardly from a surface of the shield 10. The tab could extend from an edge of the shield, but placement on a surface permits easier access thereto while reducing the possibility of inadvertently injuring an internal organ while attempting to retrieve the shield.

In essence, the shield is inserted into a body cavity and spread over the area in which the surgical procedure is to be placed thereby effectively "draping" the internal organs which are not involved in the surgical procedure. The procedure can then be performed without adversely affecting the "draped" body parts.

Figure 2:
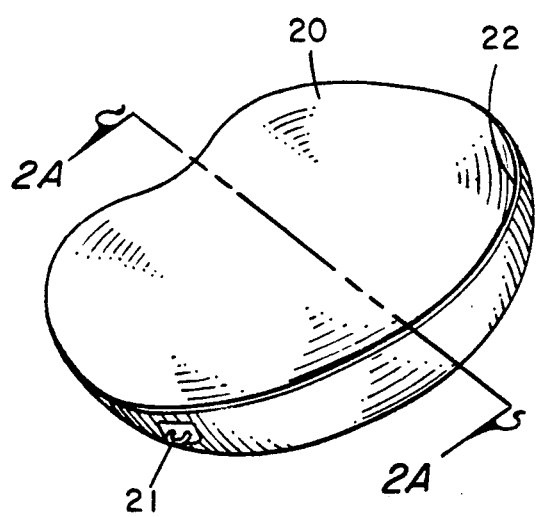
FIG. 2 is an isometric view of a shield having a different configuration and including a pocket.

Referring now to FIG. 2, there is shown another embodiment of the shield of the instant invention. In this embodiment, the shield 20 has a generally kidney-shaped, planar form. In addition, the shield 20 includes a pocket 22 which is formed by folding over a portion of the shield 20. Alternatively, a second piece of material similar to the material of shield 20 can be adhered to shield 20 through any appropriate means. For example, one edge of the pocket piece 22 can be adhered to the shield by sonic welding, thermal bonding or a suitable adhesive, as is deemed appropriate.

A handle 21 is also adhered to the shield 20. In the particular embodiment shown in FIG. 2, the handle 21 is adhered to the pocket portion 22. However, this is not an essential disposition thereof.

The pocket 22 is provided on the shield 20 in order to act as a catch-all or catch-basin for any effluvia generated during the surgical procedure. This can include blood, gore, irrigation products or the like. Thus, this unwanted, noxious material is removed from the body cavity without the necessity of special suctioning and the like.

Of course, it is possible that the material can be accumulated in the pocket and removed by merely suctioning the pocket so that the shield is not overly large during the retrieval process and/or the material is not spilled from the pocket during the retrieval process.

Figure 2A:
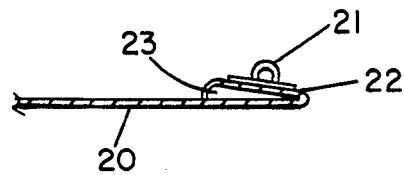
FIG. 2A is a cross-sectional view of the shield shown in FIG. 2.

Referring now to FIG. 2A, there is shown a cross-sectional view of shield 10 taken along the lines 2A—2A in FIG. 2. In this embodiment, the pocket 22 is formed as an integral part of shield 20. That is, the sheet of material for, shield 20 is folded over and joined to the sides of sheet 20. A pocket cavity 23 is formed therebetween. The handle 21 is mounted on pocket 22 in this embodiment. The handle 21 can be mounted at any desired location on the shield.

Figure 3:
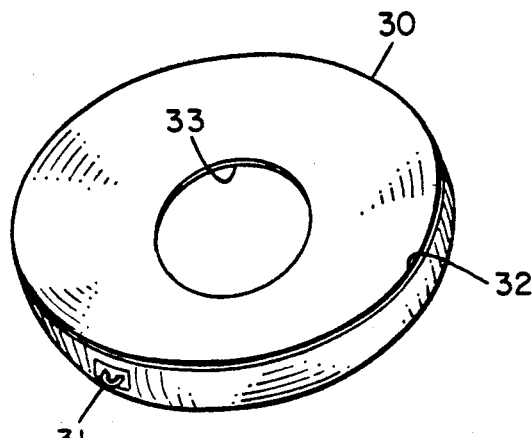
FIG. 3 is an isometric view of a shield having yet another configuration and including a pocket and an aperture therethrough.

Referring now to FIG. 3, there is shown another shield 30. In the case of this shield, the configuration is, generally, circular or oval. In addition, the shield 30 includes a pocket 32 similar to the pocket 22 shown and described relative to FIG. 2. The handle or retrieval tab 31 is also a affixed to the shield 30 directly or on the pocket 32, as shown.

In addition, shield 30 includes a central aperture 33 therethrough. Thus, the shield 30 is known as a "fenestrated" shield. Of course, it is possible to use the fenestrated shield without a pocket 32.

Figure 4:
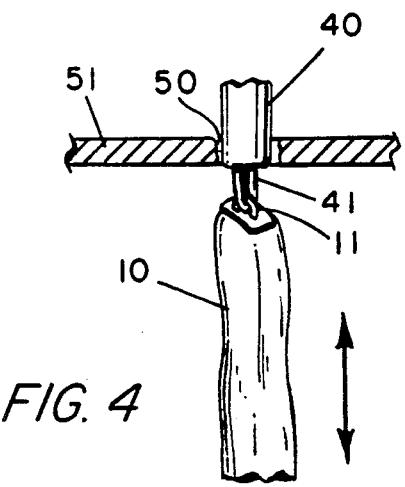
FIG. 4 is a representative illustration of the method of inserting and/or extracting a shield through a cannula passing through the skin of a patient.

Referring now to FIG. 4, there is shown a schematic representation of the insertion and removal of a shield 10 in accordance with the instant invention. The retrieval tab 11 is included with the shield 10.

In FIG. 4, the retrieval tab 11 is held between the jaws of a suitable clip or clamp 41 of conventional configuration. The clamp 41 extends through a hollow tube or cannula 40, a portion of which is shown. The cannula 40 passes through an opening 50 which has been formed in the skin layer 51, which is shown schematically. As suggested by the arrow in FIG. 4, shield 10 can be moved in or out through the skin via the cannula 40. When the shield 10 is inserted into the body cavity, it is spread out and disposed over the appropriate organs or internal viscera adjacent to the area which is to be the subject of the surgical procedure.

When the shield is retrieved, the clamp 41 is merely inserted through the cannula; maneuvered to clamp the retrieval tab 11; and removed by pulling the clamp and the shield through the cannula 40.

As noted above, when the shield is in place, the internal organs and/or viscera are protected from other laparoscopic or thoracoscopic instruments, or any of the other fluids or materials which are generated during the surgical procedure.

Thus, there is shown and described a unique design and concept of a protective intrathoracic/intra-abdominal shield. The particular configuration shown and described herein relates to a medical device, namely a shield, used in laparoscopic medical procedures. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A medical shield for use during a surgical procedure comprising,
   a thin, planar element formed of a non-toxic, membrane-like material which does not react to internal bodily fluids,
   said element is relatively flaccid so as to be manueverable through a cannula,
   said element defines a working surface.
   said element has a length between about 10 and 20 inches; a width between about 5 and 10 inches; and a thickness between about 0.5 and 2.0 millimeters.
   handle means formed adjacent said working surface of said element, and
   pocket means formed in said element to cooperate with said working surface.
2. The shield recited in claim 1 wherein, said element is formed of polypropylene.
3. The shield recited in claim 1 wherein, said element is rectilinear in configuration.
4. The shield recited in claim 1 wherein, said element is generally oval in configuration.
5. The shield recited in claim 1 wherein, said element is fenestrated with an aperture therethrough.

* * * * *